US010780200B2

(12) United States Patent
Toth

(10) Patent No.: US 10,780,200 B2
(45) Date of Patent: Sep. 22, 2020

(54) METHOD AND SYSTEM FOR REMOVING EXUDATES FROM A WOUND SITE

(75) Inventor: Landy Toth, Newton, PA (US)

(73) Assignee: CONVATEC TECHNOLOGIES INC., Las Vegas, NV (US)

(*) Notice: Subject to any disclaimer, the term of this patent is extended or adjusted under 35 U.S.C. 154(b) by 835 days.

(21) Appl. No.: 13/992,623

(22) PCT Filed: Dec. 7, 2011

(86) PCT No.: PCT/US2011/636860
§ 371 (c)(1),
(2), (4) Date: Jul. 26, 2013

(87) PCT Pub. No.: WO2012/078723
PCT Pub. Date: Jun. 14, 2012

(65) Prior Publication Data
US 2013/0304007 A1 Nov. 14, 2013

Related U.S. Application Data

(60) Provisional application No. 61/421,006, filed on Dec. 8, 2010, provisional application No. 61/421,012, filed on Dec. 8, 2010.

(51) Int. Cl.
*A61M 1/00* (2006.01)
*A61M 27/00* (2006.01)
(52) U.S. Cl.
CPC ........ *A61M 1/0049* (2013.01); *A61M 1/0031* (2013.01); *A61M 1/0072* (2014.02);
(Continued)
(58) Field of Classification Search
CPC .............. A61M 1/0049; A61M 1/0072; A61M 1/0031; A61M 2205/075; A61M 1/0011;
(Continued)

(56) References Cited

U.S. PATENT DOCUMENTS 4,850,955 A * 7/1989 Newkirk ............. A61M 27/002
604/8
5,549,584 A * 8/1996 Gross .................. A61M 1/0088
604/313

(Continued)

FOREIGN PATENT DOCUMENTS

CN 101176688 A 5/2008
CN 101678155 A 3/2010
(Continued)

OTHER PUBLICATIONS

PCT/US2011/063686 International Preliminary Report on Patentability dated Jun. 12, 2013.
(Continued)

*Primary Examiner* — Andrew J Mensh
(74) *Attorney, Agent, or Firm* — Taft Stettinius & Hollister LLP; Ryan O. White

(57) ABSTRACT

An apparatus (10) for controlling flow of fluid from a wound site of a patient may include a chamber (28) connectable to a wound site and a reservoir (16). The chamber (28) may have a first deformed state, and a second state in which it is not deformed or less deformed than in the first state. The chamber (28) may be adapted to manage fluid flow between the wound site and the reservoir (16) during transition of the chamber (28) between the first state and the second state. An actuator element (64) of the apparatus (10) may be adapted to operate on the chamber (28) to transition the chamber (28) from the second state to the first state.

23 Claims, 6 Drawing Sheets

(52) U.S. Cl.
CPC ......... *A61M 1/0009* (2013.01); *A61M 1/0011* (2013.01); *A61M 1/0023* (2013.01); *A61M 1/0066* (2013.01); *A61M 27/00* (2013.01); *A61M 2205/075* (2013.01); *A61M 2205/8206* (2013.01); *A61M 2209/088* (2013.01)

(58) Field of Classification Search
CPC .. A61M 1/0023; A61M 1/0066; A61M 27/00; A61M 1/0009
USPC ........................................................ 604/321
See application file for complete search history.

(56) References Cited

U.S. PATENT DOCUMENTS

| | | | | |
|---|---|---|---|---|
| 6,067,668 | A | * | 5/2000 | Rudd .................. E03D 9/00 4/255.01 |
| 2002/0013545 | A1 | * | 1/2002 | Soltanpour ......... A61F 9/00781 604/9 |
| 2002/0072702 | A1 | * | 6/2002 | Quay ................ A61B 5/14546 604/74 |
| 2004/0011356 | A1 | * | 1/2004 | Sullivan ............ A61M 15/0028 128/200.14 |
| 2007/0055209 | A1 | | 3/2007 | Patel et al. |
| 2008/0108977 | A1 | * | 5/2008 | Heaton ................ A61M 1/0011 604/543 |
| 2009/0157016 | A1 | | 6/2009 | Adahan |
| 2009/0281526 | A1 | | 11/2009 | Kenny et al. |
| 2011/0190735 | A1 | * | 8/2011 | Locke ................ A61M 1/0058 604/543 |
| 2011/0288511 | A1 | * | 11/2011 | Locke ................ A61M 1/0001 604/319 |

FOREIGN PATENT DOCUMENTS

| | | |
|---|---|---|
| GB | 2465797 A | 6/2010 |
| JP | 2010/525916 | 7/2010 |
| WO | WO2006/131740 | 12/2006 |
| WO | WO2007/012860 | 2/2007 |
| WO | WO2008/135997 | 11/2008 |
| WO | WO-2010006182 A2 | 1/2010 |
| WO | WO-2011094410 A2 | 8/2011 |
| WO | WO2012/078723 | 6/2012 |

OTHER PUBLICATIONS

PCT/US2011/063686 International Search Report dated Mar. 20, 2012.
PCT/US2011/063686 Written Opinion dated Mar. 20, 2012.
Chinese Patent Application No. 201180067111.9 Third Office Action dated May 12, 2016.
Chinese Patent Application No. 201180067111.9 Fourth Office Action dated Dec. 16, 2016.
Chinese Patent Application No. 201180067111.9 Office Action dated Apr. 7, 2017.
Canadian Patent Application No. 2,819,472 Examination Report dated Oct. 4, 2017.
Chinese Patent Application No. 201180067111.9 Fifth Office Action dated Sep. 29, 2017.
Chinese Patent Application No. 201180067111.9 Reexamination Decision dated Sep. 11, 2017.
European Patent Application No. 11847193.7 extended European Search Report dated Nov. 14, 2017.
Canadian Patent Application No. 2,819,472 Examination Report dated Jun. 15, 2018.

* cited by examiner

METHOD AND SYSTEM FOR REMOVING EXUDATES FROM A WOUND SITE

CROSS-REFERENCE TO RELATED APPLICATIONS

The present application is a U.S. National Phase of International Application No. PCT/US2011/63686, filed on Dec. 7, 2011, which claims benefit of the filing date of U.S. Provisional Application No. 61/431,012, filed Dec. 8, 2010, entitled "Method and System for Removing Exudates from a Wound Site", and U.S. Provisional Application No. 61/421,006, filed Dec. 8, 2010, entitled "System and Method for Applying Oscillating Pressure to a Wound Site", the disclosures of which are hereby incorporated herein by reference.

BACKGROUND OF THE INVENTION

Typical systems for removing exudates from a wound site can be bulky, low capacity and/or passive. As a result, the systems cannot be readily portable or provide satisfactory exudate management. Also, typical systems can be prone to leak failures, thus rendering them less useful for use on even moderately sized wounds. Further, typical systems having an air-based pump can be too large, expensive and inefficient to be usable in wearable applications.

For example, a typical bulky system for removing exudates uses air-based accumulators that move a lot of air to sustain a vacuum, and has a large container with a gravity trap for exudates, which increases the size of the system independent of the amount of exudate being removed. Such systems typically can introduce leaks into the fluid flow lines of the system, and also overcompensate on power capability to ensure a vacuum is maintained in the presence of a substantial leak. Further, such systems usually are designed to handle the largest expected wounds, and to have a large configuration.

Typical low capacity systems for removing exudates, although being more portable, have very small containment systems. Such smaller containment systems often may not be sufficiently large enough to hold the volume of exudates liberated daily from moderately or highly exuding wounds. In many cases, the containment systems cannot hold more fluid than a moist wound dressing.

Further, typical passive systems for removing exudates, which have spring-loaded canisters and apply a vacuum until the canisters become full or until a leak forms at a dressing, can be very leak prone, such as at connectors, around dressing seals, etc. Also, typical passive systems cannot apply a vacuum intermittently. The passive systems further can include disposable canisters, such that they are not environmentally friendly.

Therefore, there exists a need for a system for removing exudates from a wound site which is portable, may be manufactured under less demanding component tolerances, may be of relatively small size, may sustain therapy in the event of a leak, may provide effective intermittent vacuum therapies and may provide therapy for larger wounds.

BRIEF SUMMARY OF THE INVENTION

In accordance with an aspect of the invention, an apparatus for controlling flow of fluid from a wound site of a patient may include a chamber connectable in fluid communication with the wound site and a reservoir for receiving and holding fluid. The chamber may have a first state, in which the chamber is deformed, and a second state, in which the chamber is not deformed or less deformed than in the first state. The chamber may be adapted to manage fluid flow between the wound site and the reservoir during transition of the chamber between the first state and the second state. In addition, the apparatus may include an actuator element adapted to operate on the chamber to transition the chamber from the second state to the first state.

In accordance with another aspect of the invention, an apparatus for controlling flow of fluid from a wound site of a patient may include a passive pump unit including a chamber having an input for receiving the fluid from the wound site of the patient conveyed over a conduit connectable in fluid communication with the input and an output for providing the received fluid from the chamber. The apparatus may further include an actuator element operable to create a pressure within the chamber for drawing the fluid from the wound site through the conduit and the input and into the chamber. The chamber may be adapted to hold the received fluid without the received fluid flowing through the input and the output, and to provide the received fluid from the chamber through the output without the received fluid flowing through the input.

DETAILED DESCRIPTION

Figure 1:
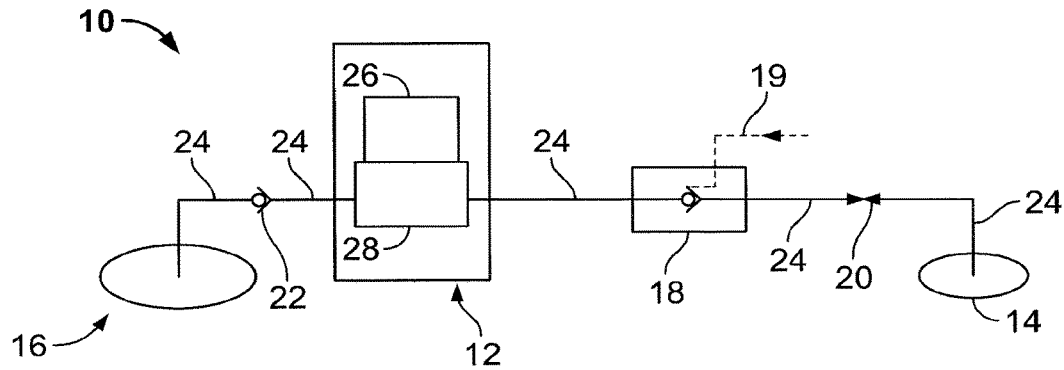
FIG. 1 is a block diagram of a system for removing exudates from a wound site, in accordance with an aspect of the invention.

FIG. 1 illustrates a system 10 for removing exudates from a wound site, in accordance with an aspect of the present invention. Referring to FIG. 1, the system 10 may include an apparatus 12 for controlling flow of fluid from a dressing 14 that may be applied to a wound site of a patient, a reservoir 16 for receiving and holding exudates and fluid from a wound site, a one-way inlet valve 18, a one-way outlet valve 22 and an optional closure device 20. The apparatus 12 may be connected, using conduits 24, to be in fluid communication with the wound site through the inlet valve 18 and the closure device 20, and to be in fluid communication with the reservoir 16 through the outlet valve 22.

In one embodiment, the reservoir 16 may be a collapsible chamber that slowly expands as it fills with exudates and fluid. In addition, the reservoir may be in the form of a bag, and may be adapted to couple to clips, bands or the like that may be used to fasten the bag-shaped reservoir to clothing, a patient's appendage or a bedside table, etc., during use. In another embodiment, the reservoir may include a filter for gas liberation, and a charcoal filter to minimize odor.

In one embodiment, the conduits 24 may be tubes formed using film processes or by extrusion processes. For example, the conduit may be a flexible conduit adapted not to collapse during use. In addition, the conduits may include odor barriers to reduce smell during use of the inventive system. In another embodiment, the conduits may be flat, thermoformed channels.

In a further embodiment, one or more of the conduits may be formed from two flat strips of thin flexible material welded or bonded together along their long edges to form a channel. The channel may also contain one or more spacer strips welded or bonded to the walls of the channel to ensure a fluid path is maintained even when the channel is folded or crushed or subjected to a vacuum pressure. The advantage provided by this feature is that the channel is low profile and lightweight to assist with portability and discretion. See, for example, PCT/GB2006/002806 and PCT/GB2006/002097, incorporated by reference herein.

The outlet valve 22 may be arranged in the system 10 to permit fluid flow only in a direction from the apparatus 12 to the reservoir 16. The inlet valve 18 may be arranged in the system 10 to permit fluid flow only in a direction from the dressing 14 to the apparatus 12. The valves 18 and 22, which are inline to the flow to and from the apparatus 12, may seal upon application of back pressure, such as may occur during a process to purge material from within the apparatus 12 and cause the purged material to be conveyed to and into the reservoir 16. Exemplary valves may include flap valves, flappers, flanges, anti-reflux valves, ball valves, duck bill valves, etc.

In one embodiment, the valve 18 may include a pilot valve that automatically, when pressure in one direction closes the valve, does not allow flow, and when there is pressure in the opposite direction, immediately opens the valve and allows flow. In an alternative embodiment, the pilot valve 18 may remain positively closed in either direction, or open in a desired direction only upon application of a separate pilot signal 19. The pilot signal 19 may be an electrical signal, such as from a controller of the apparatus 12, to open the valve. Alternatively, the pilot signal 19 may be based on fluid pressure increasing to a certain level through a pilot port, which then fully opens a main valve.

In another embodiment, the one-way valves 18 and 22 may be optimized to avoid their becoming obstructed by gels, proteins and solid masses in the fluids being communicated therethrough.

The closure device 20 may be a valve operable to prevent fluid flow in any direction therethrough, and also permit fluid flow therethrough in a single direction, such as from the dressing to the apparatus 12.

The apparatus 12 may include a pump element 26 associated with an inline, self-filling pump cavity or chamber 28. The pump element 26 may be an active or mechanically operated component which may operate to create a pressure or a vacuum in the pump cavity, so as to draw exudates from a wound site into the pump cavity and to force exudates being retained in the pump cavity from the pump cavity into a storage element, such as the reservoir 16.

Figure 2:
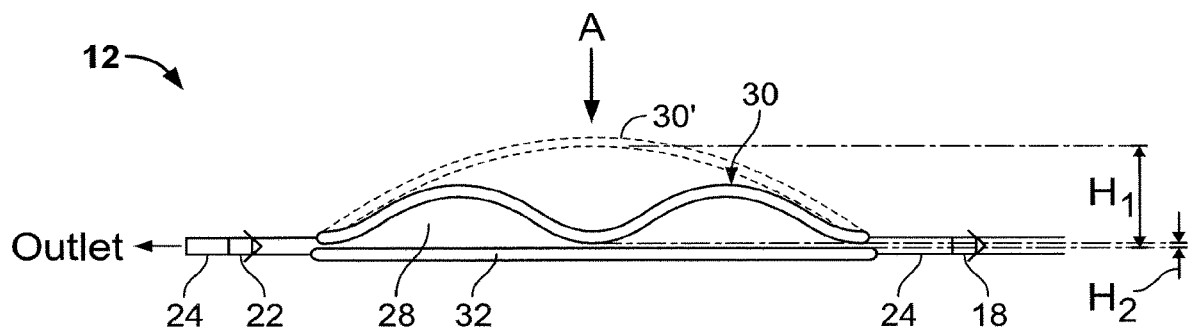
FIG. 2 is a schematic, cross-sectional view of an apparatus for controlling fluid flow from a wound site, in accordance with an aspect of the invention.

Referring to FIG. 2, in one embodiment the apparatus 12 may include a deformable top wall 30 opposing a rigid or substantially non-deformable back plate 32, which in combination form a self-filling cavity or chamber 28. The top wall 30 may recover its original shape after being deformed in the direction of the back plate, and include resilient material. The top wall 30, when in a non-deformed state as indicated by dashed lines 30' in FIG. 2, or a partially deformed state, may be acted upon to become deformed or further deformed to obtain a desired deformed state. The top wall 30 may be deformed, for example, by applying a force on the top wall 30 in a direction indicated by arrow A, toward the opposing base plate 32, to cause a portion of the top wall 30 to deform and move in the direction of the base plate 32. When the top wall 30 is deformed, a distance or height between a portion of the top wall 30 that is deformed and an opposing portion of the base plate 32 decreases, respectively, from a height H1 to a height H2 as shown in FIG. 2. The deformation of the top wall 30 reduces the space between the deformed portion of the top wall 30 and the base plate 32, thereby reducing the volume of the cavity 28 defined by the combination of the top wall and base plate. As the valve 18 in communication with the inlet of the cavity 28 prevents fluid flow from the apparatus 12 toward the dressing 14, when the top wall 30 is being deformed, contents, such as fluid or exudate from a wound site retained within the cavity, may be forced through the valve 22 and into the reservoir 16. The emptying of the contents from within the cavity may be part of a purging process performed at the apparatus 12.

When a force acting upon the top wall 30 is released after the top wall 30 is deformed by application of such force, such as shown in FIG. 2, the top wall 30 may begin to recover its original non-deformed shape during a recovery process, in which the deformed top wall is permitted to become less deformed and return to its non-deformed state. As the top wall 30 becomes less deformed and is transitioning from a deformed state to a less deformed state and ultimately its non-deformed state, the volume of the cavity 28 increases. During the recovery process, a vacuum or pressure in the cavity 28, which was created based on deformation of the top wall 30, may act through the valve 18 to draw fluid and exudates from the wound site, to which the cover dressing is applied, into the cavity. Thus, the cavity, which is inline to flow of fluid from the wound site and also to the reservoir, may act as a passive pump that draws fluid from the wound site. Advantageously, the cavity of the apparatus 12 may maintain a vacuum therein between reset procedures, during which the top wall 30 is caused to become deformed or more deformed, in the absence of any action by or manipulation of the components of the apparatus 12.

Figure 3:
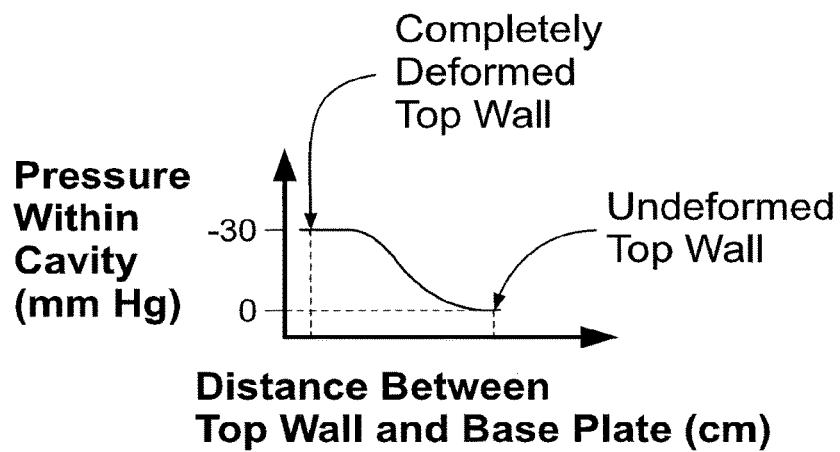
FIG. 3 is a graph illustrating a relationship between pressure and extent of deformation for the apparatus of FIG. 2.
Figure 16:
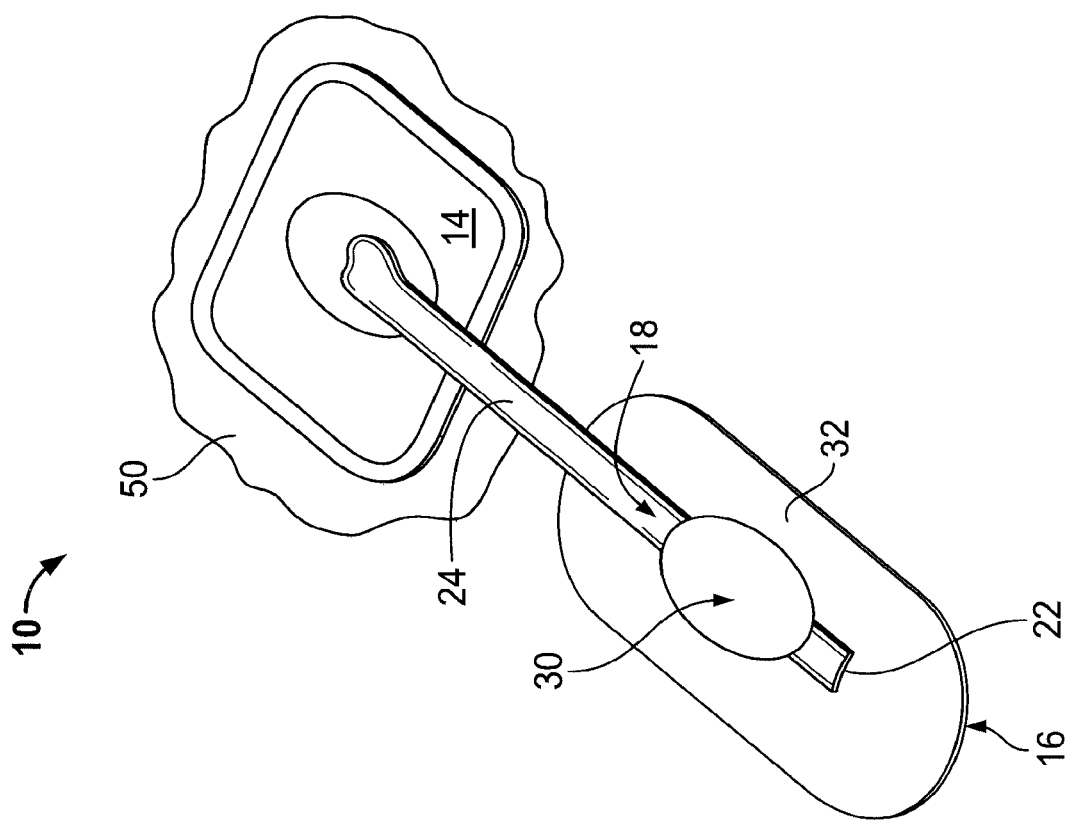
FIG. 16 is a schematic, plan view of a system for removing exudates from a wound site in an operative state, in accordance with an aspect of the invention.

Referring to FIG. 3, the deformation of the top wall 30 from its non-deformed state to a completely deformed state may result in a pressure within the cavity being changed from 0 to −80 mm Hg. In other words, a vacuum may be created internally within the cavity based on deformation of the top wall. Such vacuum may cause exudates to be drawn from the wound site into the cavity during a recovery process when the top wall is returning to its non-deformed state. FIG. 16 illustrates an exemplary implementation of the system 10 at a wound site 50 for drawing fluid from the wound site 50 into the reservoir 16.

In one embodiment, the cavity 28 may have a diameter of about 50 mm, and be adapted such that the top wall is spaced from the bottom plate about 5 mm and 10 mm when, respectively, 10 ml and 20 ml of exudate is contained within the cavity. In one embodiment, the cavity may have a one inch diameter and be operable to maintain a vacuum at −80 mm Hg.

Figure 4:
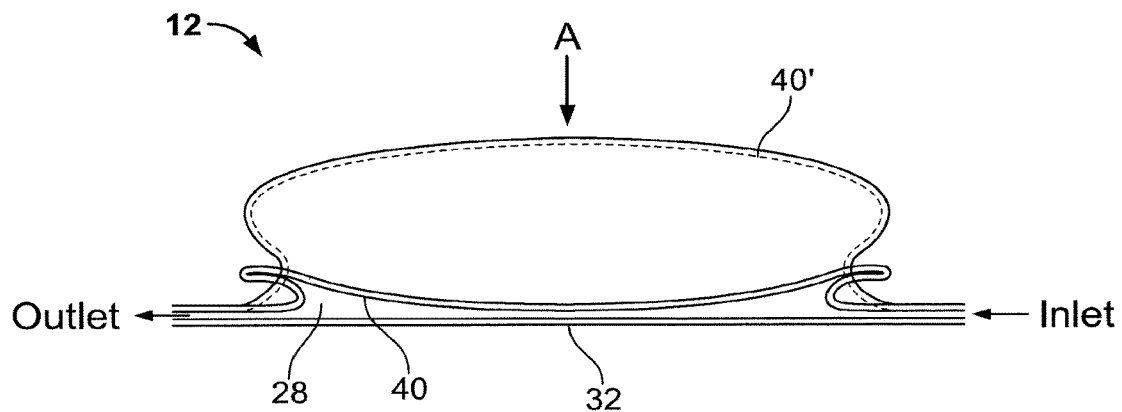
FIG. 4 is a schematic, cross-sectional view of an apparatus for controlling flow of fluid from a wound site, in accordance with an aspect of the invention.

Referring to FIG. 4, in an alternative embodiment, the apparatus 12 may include a deformable top wall 40 adapted such that, when a force is applied to the top wall 40 in the direction A toward the base plate 32 when the top wall 40 is in its non-deformed state as indicated by dashed lines 40', substantially the entirety of the wall 40 opposing the base 32 may become deformed.

Figure 5:
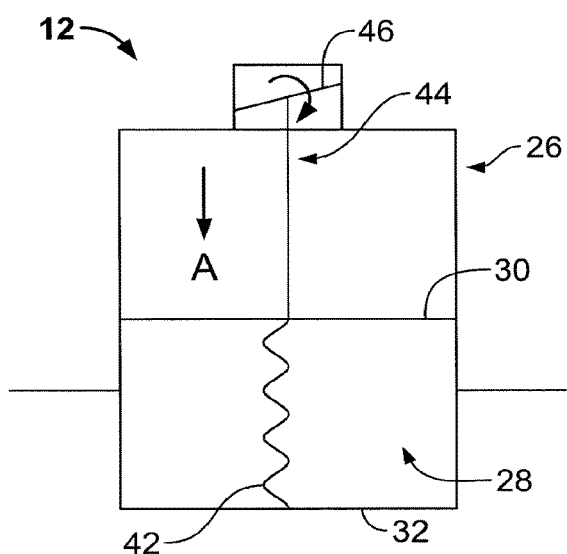
FIG. 5 is a schematic, cross-sectional view of an apparatus for controlling flow of fluid from a wound site, in accordance with an aspect of the invention.

Referring to FIG. 5, in another embodiment the apparatus 12 may include a spring element 42 extending between the top wall 30 and the base plate 32 that in combination form the cavity 28. The spring element 42 may serve as an additional support for the cavity 28, so as to maintain the cavity at a desired maximum volume state, which may be obtained when the top wall is in the non-deformed state. The pump element 26 may include a plunger device 44 that is mechanically operable, by application of a force on a handle 46 of the plunger device 44, to apply a force in the direction A on the top wall 30, so as to deform the top wall 30 in the direction of the bottom plate 32, similarly as described above.

In one embodiment of the system 10, the conduits 24, the cavity portion of the apparatus 12 and the reservoir 16 may be combined into a single unit that is disposable with no air entrainment. For example, the system 10 may be supplied in an fully assembled state with the reservoir empty and the flexure pump chamber pre-collapsed, such that when the dressing 14 is applied to a wound site and the system 10 is activated, the pump chamber 28 expands to draw fluid from the wound site without first expelling air from the pump chamber into the reservoir 16.

In a further embodiment, the system 10 may be adapted to be air free, so as to decrease escape of odors from microleaks in joints and seals. Advantageously, the absence of air in the system 10 may improve efficiencies of the micropump, and also improve control of conduit barrier properties, in that air is more compressible than liquid and therefore more energy usually is expended to achieve a desired pressure in a system with air entrained than in one without.

In a further embodiment, the cavity 28 may include or be formed from absorptive filler material, similar to material used in the dressing applied to a wound site. The absorptive filler material of the cavity may include open cell foams, alginates, hydrofibers, CMC based materials and hydrocolloids. Desirably, the filler material can store fluids in a liquid form or absorb the wound fluid and form a gel to retain the exudate. In one embodiment in which the system 10 is used with the reservoir 16, the filler material may be a foam, which permits the fluid to be held as a fluid and then displaced into the reservoir when the pump chamber is compressed. In an embodiment in which the cavity 28 is of filler material that forms a gel, the system 10 may be used without the reservoir 16 and the non-return valve 22, such that the system 10 can be discarded when the pump chamber becomes full.

In one embodiment, the entire system, including the conduits, the passive pump apparatus including the cavity and pump element, valves and reservoir, may be made using a roll to roll process, such as with a tubular sheath at the outlet for attachment to a cover dressing. In one embodiment, all of the elements of the system may be made from relatively thin sheet materials which are unrolled, cut or perforated, and bonded together to form the different connected elements and then wound back onto a roll as a finished item, such that the system can be dispensed from the roll. Such system advantageously may have a very low cost construction, and minimizes packaging materials.

Figure 6:
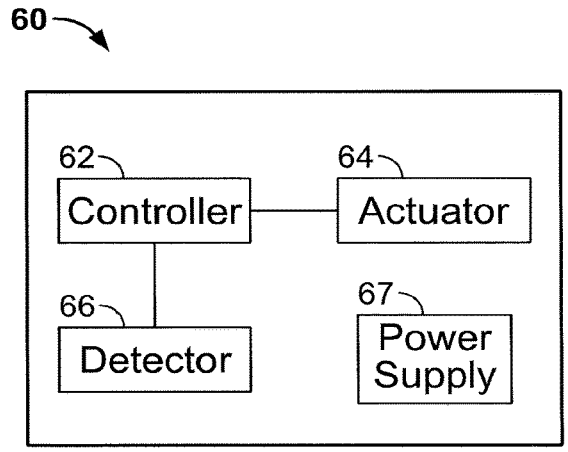
FIG. 6 is a block diagram of a fluid flow control device for use in an apparatus for controlling flow of fluid from a wound site, in accordance with an aspect of the invention.

In another embodiment, referring to FIG. 6, the apparatus 12 may be adapted to include an active element 60 operable to create or re-establish a vacuum within the cavity 28 of the apparatus 12. The active element desirably is arranged external to the cavity, so as to be isolated from fluids and exudates being held within and conveyed to and from the cavity, and thus prevent biofouling of the components of the active element. The active element 60 may include a controller 62 electrically coupled to an actuator device 64 and a proximity detector 66.

The proximity detector 66 may be a sensor, such as an infrared (IR) detector, that detects distance between the detector and an opposing object, such as the top wall 30. The detector 66 may provide detection information representative of the detected distance to the controller 62.

The controller 62 may include a processor and a memory including instructions executable by the processor to control actuation of the actuator device 64 based on detection information from the proximity detector 66. The instructions in the memory may also provide for active control of pressure within the cavity, by controlling operation of the actuator device 64. In addition, the active element may include a power supply 67, such as a battery, for providing electrical power to the components within the active element.

Figure 7:
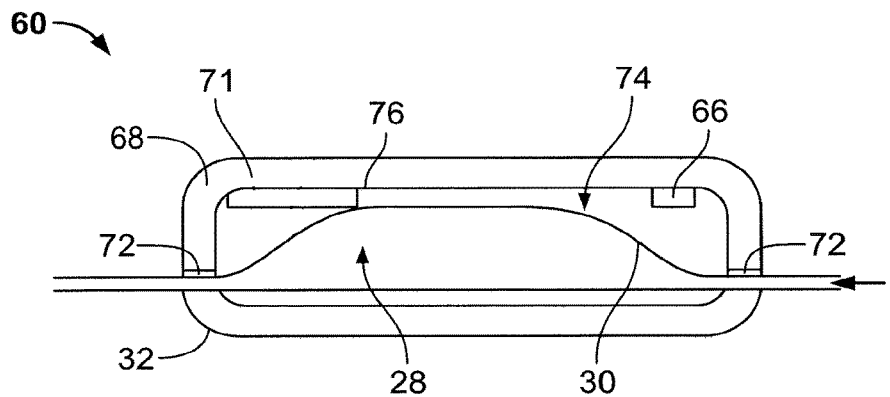
FIG. 7 is a schematic, cross-sectional view of an apparatus for controlling flow of fluid from a wound site, in accordance with an aspect of the invention.

Referring to FIG. 7, the active element 60 may be a part of or integrated with an outer wall 68 attached by seals 72 to the back plate 32. The outer wall 68 and the back plate 32, in combination, may define a sealed chamber 74 which is in fluid communication with the top wall 30 of the cavity 28. In one embodiment, the actuator device 64 may be an electronic micropump 71 attached to an interior surface 76 of the outer wall 68 and having an outlet (not shown) in fluid communication with the chamber 74. The pump 71 may be a miniature air pump or a reciprocating pump, or desirably a very compact low weight, low energy pump based on active material actuation technology, such as including a piezo ceramic material.

The controller 62 may operate the micropump 71 to create a desired pressure, such as positive pressure or a vacuum, within the chamber 74. The creation of a positive pressure within the chamber 74, in turn, may cause the top wall 30 to deform and, thus, compress the cavity 28 to create a vacuum within the cavity 28. Alternatively, the creation of a vacuum within the chamber 74 may cause or allow the top wall to become less deformed or return to its non-deformed state.

In one embodiment, after the top wall transitions to a less deformed or its non-deformed state, such as may occur when a leak is formed at the dressing attachment to the wound site, the controller may cause the pump 71 to create a positive pressure in the chamber 74 to re-start withdrawal of exudate from a wound site, after the leak that formed at the dressing attachment to the wound site has been sealed.

In an exemplary operation of the apparatus 12, the active element 60 may control the micropump 71 to maintain or change pressure within the chamber 74 to ensure that either continuous or intermittent vacuums are applied to the wound site, while a primary vacuum is sustained at the wound site based on the configuration of the cavity. The primary vacuum is a function of the extent that the top wall is or has been deformed. The cavity, thus, may serve as a passive pump that can be acted upon by the active element 60, such as based on controlled operation of the micropump 71, so that a vacuum is continuously or intermittently applied to the wound site. Advantageously, the active element 60 may operate to reset or re-prime the passive pump during a reset process, in other words, to re-establish a desired pressure within the cavity 28, by suitably creating a positive pressure in the chamber 74. The reset process functionality of the active element may permit the apparatus 12 to continue to operate even if a leak is developed at the wound site, which may cause a vacuum within the cavity, which is in fluid communication with the wound site, to be at least partially lost.

In one embodiment, during a process to reset the passive pump, exudates collected within the cavity may be forced from the cavity, through the valve 22 and into the reservoir 16, and the vacuum within the cavity 28 may be re-established by creating a positive pressure within the chamber 74.

The valves 18 and 22 may provide for a desired direction of fluid flow in the system 10, such as movement of fluid from the wound site, through the apparatus 12 including a pumping means, to the reservoir, and avoid fluid from being pushed back to the wound site when resetting the actuator device. In one embodiment, the size and configuration of the chamber 74 and the cavity 28, and the capacity of the pump 71, may be designed to optimize the reset process. In one embodiment, the cavity and the reservoir may be independently optimized. For example, the reservoir may have a low profile and become filled to accommodate only the amount of exudate liberated from the wound. In one embodiment, the reservoir may be arranged so that a sum of the volume of the reservoir and volume of fluid in the reservoir is less than 25%, less than 15% or less than 10% greater than the volume of the fluid.

In a further embodiment, the detector 66 may be attached to the interior surface 76 of the outer wall 68 to oppose a portion of the top wall 28 that may become deformed. The controller 62 may, based on detection information provided by the detector 66 indicating the distance between the opposing portion of the top wall and the detector, determine when the cavity is full or nearly full of exudate, and also monitor the rate at which the cavity 28 fills with exudate. Depending on a determination of the extent the cavity is filled with exudate, the controller may control the pump 71 to generate positive pressure within the chamber 74, to cause the contents of the cavity to empty into the reservoir 16 and create a vacuum within the cavity, which can result in additional exudate to be drawn from the wound site to the cavity.

In another embodiment, the controller 62 may use detection information obtained from the detector 66 to assess exudate evolution rates and detect leaks at the dressing 14. Also, the controller 62 may provide for a controlled rate of return of exudates to optimize vacuum pressure levels in the passive pump cavity.

Advantageously, the evolution rates and leak detection may be determined by a device, in particular, the active element 60, which is maintained isolated from fluids and exudate drawn from the wound site, and which also may be a separate and re-usable part of the system. The isolation of the active element may provide for reduced cost in terms of disposable and non-disposable elements of the system.

In one embodiment, in an apparatus adapted to have low energy consumption, the active element 60 may utilize less rigorous seals 72, or no seals may be needed on the active element, due to the ease with which pressure within the cavity may be reset using the micropump. In such embodiment, although more energy is used to reset pressure, a higher cost associated with manufacture of the apparatus with seals that make the apparatus relatively leak free, and difficulties with reliably manufacturing a leak free apparatus, may be avoided.

Also, the system of the invention may be made sufficiently small and portable, and also sized according to patient need, independent of the size of the micropump.

In a further embodiment, referring to FIGS. 5 and 6, an active element 60 may be included in the apparatus 12, and the actuator device 64 may be a solenoid operable by the controller to force the plunger 44 in the direction A to deform the top wall 30 and thus create a vacuum in the cavity 28.

Figure 8:
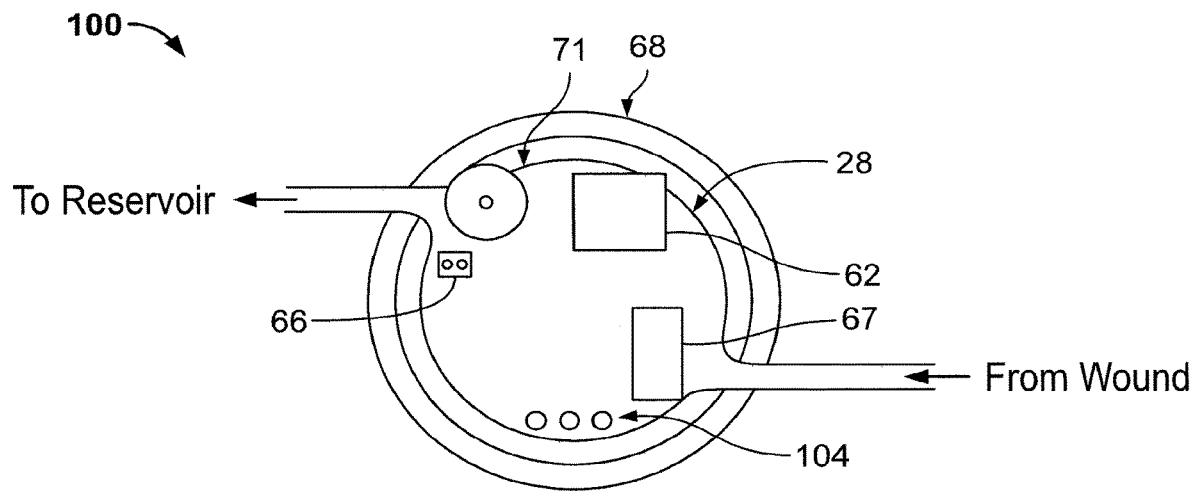
FIG. 8 is a schematic, plan view of an apparatus for controlling flow of fluid from a wound site, in accordance with an aspect of the invention.
Figure 9:
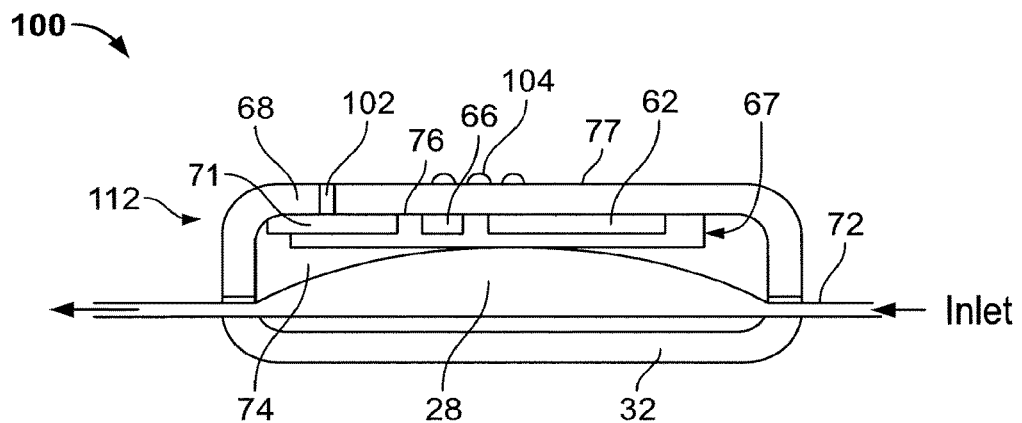
FIG. 9 is a schematic, cross-sectional view of the apparatus of FIG. 8.

In one embodiment, referring to FIGS. 8 and 9, a system for removing exudates from a wound site 100 may contain a flow control apparatus 112 including components that are the same or substantially similar to those of the apparatus 12 of the system 10 described above. Like reference numerals are used to describe the same components in the system 10 contained in the system 100. Referring to FIGS. 8 and 9, the apparatus 112 may include a micropump 71, a controller 62, a proximity detector 66 and a battery 67 attached to the interior surface 76 of the outer wall 68 of the apparatus 112. The apparatus 112 further may include a vent 102 extending through the thickness of the outer wall 68 to an outlet port (not shown) of the micropump 71. In addition, the apparatus 112 may include indicators 104, such as LEDs, attached to an outer surface 77 of the outer wall 68 and electrically connected to the controller 62. The controller 62, based on detection information provided by the detector 66, may cause the LEDs 104 to illuminate, for example, based on a determined evolution rate or a determination that the outer wall is not transitioning between a deformed and non-deformed state, as may occur if the pump 71 malfunctions or ceases to function.

In one embodiment, the controller 62 may operate to provide that mismatches between the stroke capacities of the active element, such as the micropump, and mechanical impedance to fluid flow in system components are overcome, thereby providing higher pumping efficiency.

Also, the controller 62 may operate the pump so as to optimize electrical power utilization of the battery.

In addition, the controller 62 may cause one or more of the indicators 104 to illuminate when the controller 62 determines a low battery level.

Figure 10:
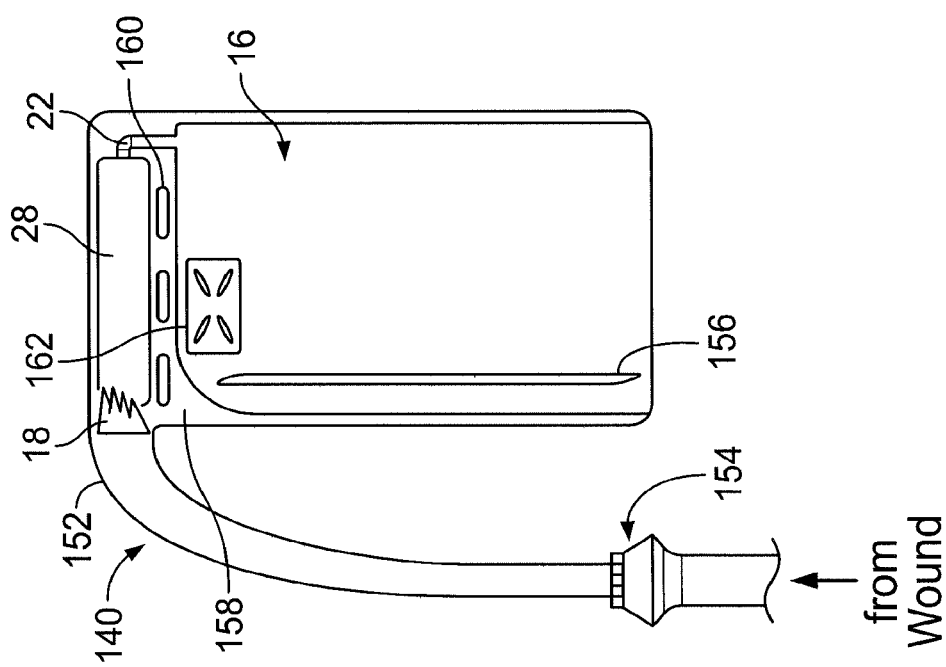
FIG. 10 is a schematic view of a system for removing exudates from a wound site, in accordance with an aspect of the invention.

In one embodiment, a system for removing exudates from a wound site 140 having the same or similar components and functionality as components of the system 10 may be adapted for mounting to an object or a patient, as illustrated in FIG. 10. Like reference numerals are used to describe like components of the system 10, as previously described. Referring to FIG. 10, the system 140 may be an integrated device including the components of the apparatus 12 and the reservoir 16. The cavity is in fluid communication with the reservoir 16 through a valve 22, and a valve 18 interconnects the cavity with a conduit 152 having an end terminated with a leak proof connector 154, which is for connection to a connector (not shown) of a dressing. The apparatus 12 may further include a reservoir level indicator 156 disposed on an outer surface of the reservoir 16 to indicate the extent to which the reservoir is filled with exudate. The level indicator 156 may be in the form of a clear window through which the interior of the reservoir may be viewed, or alternatively may be a color changing strip, such as litmus paper that changes color on contact with the fluid, or a moisture sensitive material. In addition, the apparatus 12 may include a strip 158 of material, such as pressure sensitive adhesive, silicone adhesive, hydrocolloid or hook and loop, attaching the reservoir to the cavity 28, and to which mounting clips are attached to allow the apparatus 12 to be secured to an object. Further, the system 140 may include a gas filter 162, such as a charcoal filter, adapted in relation to the reservoir so as to be bonded or glued to cover a window cut through the wall of the reservoir. In addition, the filter may have olephobic and hydrophobic properties to allow the release of gas without allowing fluids to pass through and potentially leak.

Figure 11:
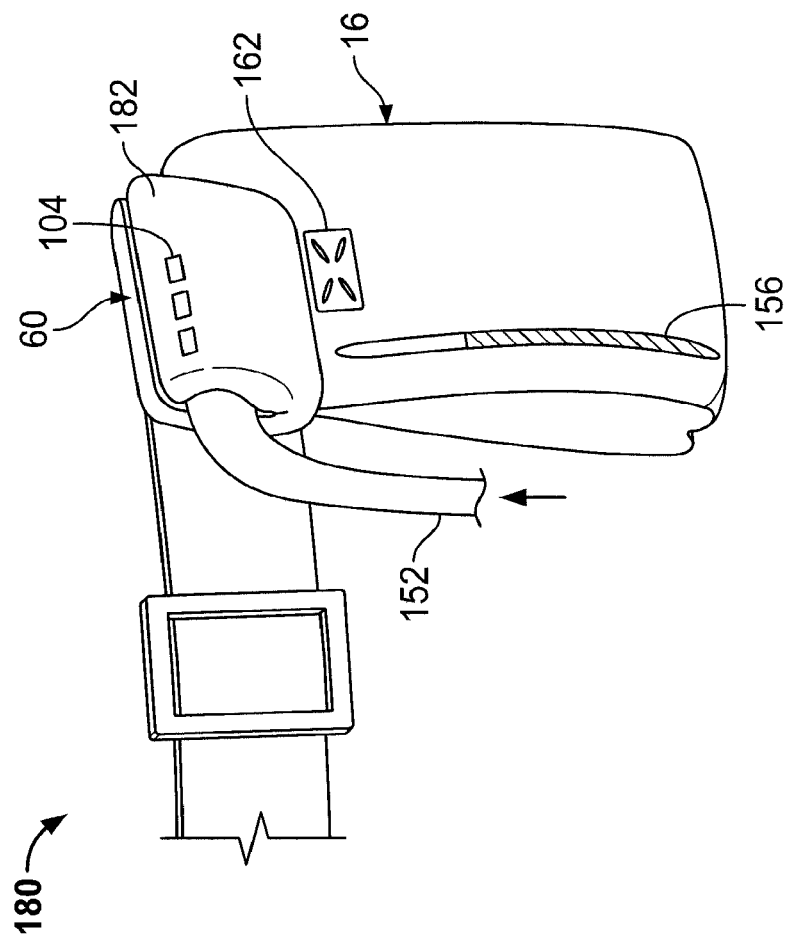
FIG. 11 is a schematic view of a system for removing exudates from a wound site, in accordance with another aspect of the invention.

In another embodiment, a system for removing exudates from a wound site 180 having the same or similar components and functionality as components of the system 100 may be adapted for mounting to a belt of a patient, such as shown in FIG. 11. Like reference numerals are used to describe like components of the system 100, as previously described. Referring to FIG. 11, the system 180 may be an integrated device including the reservoir 16 having a bag-shaped configuration, and a housing 182 containing the components of the apparatus 12 and the active element 60 and connected to the reservoir 16. The system 180 further may include LEDs 104 on an outer surface of the housing 182, a conduit 152 to be connected in fluid communication with a wound site, a reservoir fill level indicator 156 and a reservoir filter 162.

Figure 12:
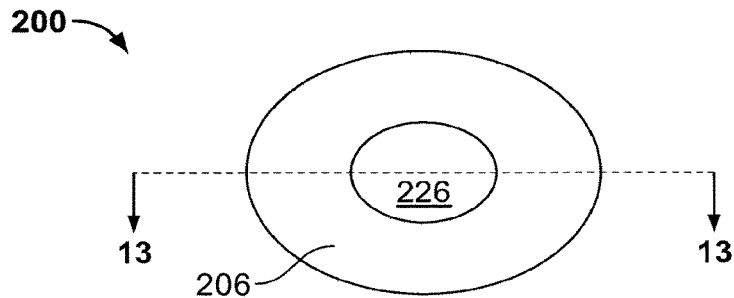
FIG. 12 is a top plan view of an apparatus for controlling flow of fluid, in accordance with aspect of the invention.
Figure 13:
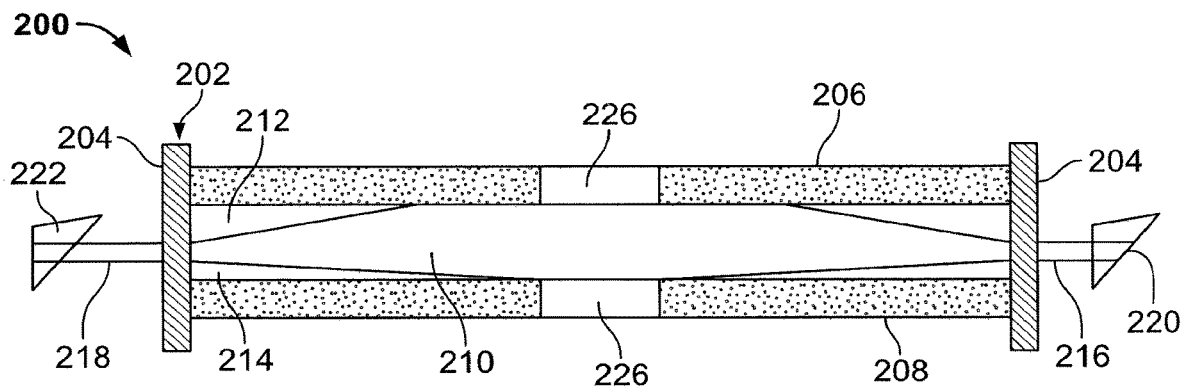
FIG. 13 is a cross-sectional view of the apparatus of FIG. 12 at line 13-13.
Figure 14:
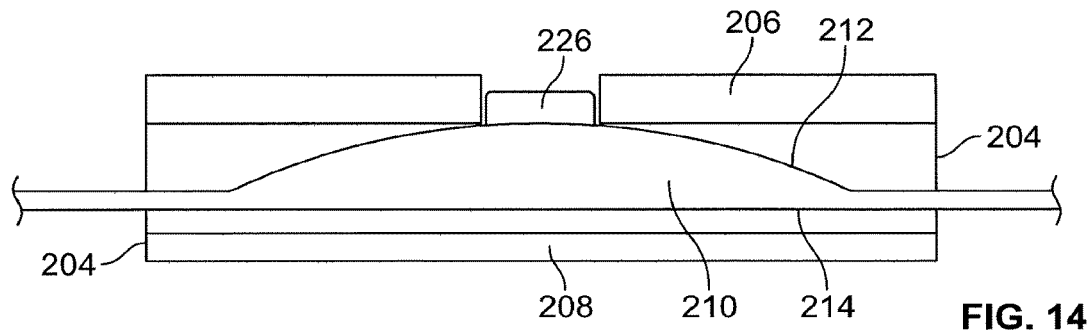
FIG. 14 is a cross-sectional view of another embodiment of an apparatus for controlling flow of fluid, in accordance with an aspect of the invention.

In another aspect, the actuator device of the apparatus of the disclosure may be a piezoelectric device arranged to act on a wall defining the self-filling cavity, so as to deform the wall and, thus, compress the cavity to decrease the volumetric capacity of the cavity and, hence, create a desired pressure or vacuum in the cavity. Referring to FIGS. 12-13, a flow control apparatus 200 may include a housing 202 having end walls 204 to which a top plate 206 and a base plate 208 are connected. The housing 202 encloses a self-filling cavity 210 defined by a top wall 212 and bottom wall 214 which connect the cavity, at an inlet port 216 and an outlet port 218, in fluid communication with respective input and outlet valves 220, 222 which are for connection to an exudate reservoir (not shown) and a dressing (not shown) to be applied at a wound site. The top plate 206 and the bottom plate 208 may include a piezoelectric device 226 disposed in relation to the top and bottom walls 212, 214, respectively, so that the top and bottom walls may be deformed when one or both of the piezoelectric devices 226 is actuated. When the device 226 is actuated, the wall opposing the device 226 is compressed, to create a vacuum in the cavity, while the housing end walls 204 maintain the actuator edges fixed during movement. As the edges are fixed during movement, the volume in the chamber is forced to be reduced when the actuators move inwards, and thus a vacuum is created to draw off the wound fluid when the actuators move outwardly to a non-actuated position.

In one exemplary embodiment, the apparatus 200 may provide that the piezoelectric device 226 is operated to vibrate at up to 1.8 KHz and cause movement of the wall of the cavity opposing the device 226 away from the device 226 a distance of about 25 microns.

In another exemplary operation of the apparatus 200, the piezoelectric devices may be used to drive a fluid coupled "reset," such as by being actuated over several cycles, similarly as described above with reference to FIG. 7 regarding actuation of a micropump using a secondary fluid to interact with a first fluid. Referring to FIG. 7, the micropump 71 evacuates the first fluid out of the cavity 74 to reset the actuator and allow a vacuum to be applied to draw fluid from the wound site into cavity 28. Although a piezo micropump may only move short distances with each cycle, for example, 47 micrometers, it can operate at a high cycle rate, such as 1.8 KHz. For each cycle, the very small movement may draw a very small amount of fluid from the chamber and push the fluid out through the hole. The spring or other bias effectively resets the chamber's position after each cycle, so that the chamber is ready for the next cycle. Advantageously, the piezo drive micropump may be very small, such as about 1 inch in diameter, and use little energy, and by operating over several cycles, a sufficient amount of fluid may be moved to create, for example, an 80 mm Hg vacuum.

In another embodiment, the base plate 208 of the apparatus 200 may include resilient material to provide a bias against the bottom wall 214 that defines the cavity 210.

Figure 15:
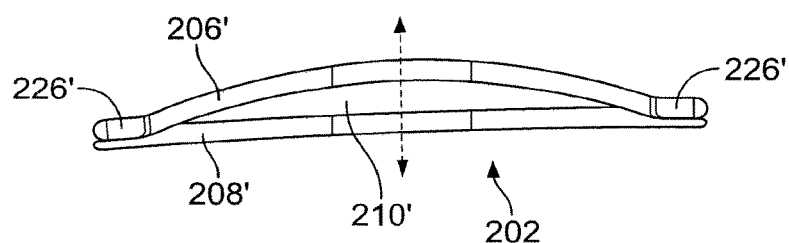
FIG. 15 is a cross-sectional view of another embodiment of an apparatus for controlling flow of fluid, in accordance with an aspect of the invention.

In another embodiment, referring to FIG. 15, the housing 202 of the apparatus 200 may include a top plate 206' and base plate 208', and piezoelectric devices 226' that interconnect the base and top plates at, or form a circumferential edge or ring, of a cavity 210'. In an exemplary operation of this embodiment, when the devices 226' are cycled between an actuated state and a non-actuated state, the circumference becomes shorter or longer causing the top and bottom plates to move outwards or inwards and, hence, the volume in the cavity increases or decreases.

Figure 17:
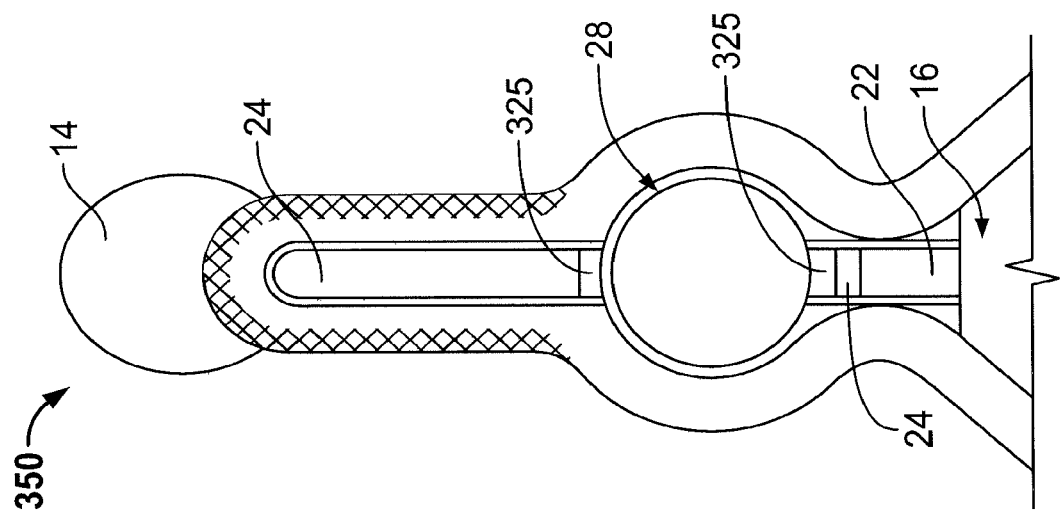
FIG. 17 is a schematic, plan view of an exemplary a system for removing exudates from a wound site, in accordance with an aspect of the invention.

FIG. 17 illustrates an exemplary system for drawing fluid from a wound site 350 that may include the same or similar components as in the system 10. Referring to FIG. 18, the system 350 may further include a pinch valve 325 at the inlet and outlet of the cavity 28 to control flow of fluid into and out of the cavity 28.

Overall, the invention advantageously may provide therapy by way of a minimally sized, airless and disposable system. The reservoir desirably may be reduced in size in relation to the expected amount of fluid to be drawn from a wound site. In addition, disposable and reusable components may be combined in a cost effective manner and to make the system practical for use in a home setting. Further, the system may be adapted to address inefficiency by controlling the amount of air moved during treatment, as suitable. Also, the system may be made environmentally sound.

Although the invention herein has been described with reference to particular embodiments, it is to be understood that these embodiments are merely illustrative of the principles and applications of the present invention. The following numbered paragraphs additionally describe embodiments of the invention as set forth herein.

The invention claimed is:

1. An apparatus, for controlling flow of thud from a wound site of a patient comprising:
   an active element including wall defining a sealed chamber and a pumps;
   a cavity disposed within the sealed chamber, the cavity configured for fluid communication with the wound site and a reservoir that receives and holds exudate, the cavity comprising an input for communication with the wound site, an output for communication with the reservoir, and a non-rigid, deformable wall in fluid communication with the sealed chamber, the non-rigid, deformable wall opposing a rigid, non-deformable plate, wherein the cavity is arranged between the wound site and the reservoir such that exudate from the wound site is drawn through the cavity and into the reservoir; the cavity having a first state and a second state, wherein the cavity is adapted to draw exudate from the wound site into the cavity and to manage exudate flow between the wound site and the reservoir during transition of the cavity between the first state and the second state, wherein the input of the cavity is not positioned at the deformable wall or non-deformable plate; and
   wherein the pump is adapted to apply a force fluid pressure to the non-rigid, deformable wall of the cavity in the direction of the rigid, non-deformable plate to transition the cavity from the second state to the first state.

2. The apparatus of claim 1, further comprising a proximity detector located in the sealed chamber to detect a distance between the proximity detector and the non-rigid deformable wall, wherein the apparatus is portable.

3. The apparatus of claim 1 further comprising the reservoir.

4. The apparatus of claim 3, wherein the reservoir is arranged so that a sum of volume of the reservoir and volume of exudate in the reservoir is less than 25%, less than 15% or less than 10% greater than the volume of the exudate.

5. The apparatus of claim 1, wherein the cavity is adapted to draw exudate from the wound site into the cavity when the cavity is transitioning from the first state to the second state.

6. The apparatus of claim 1, wherein the cavity is adapted to push exudate into the reservoir when the cavity is transitioning from the second state to the first state.

7. The apparatus of claim 1, wherein the cavity is adapted to draw exudate from the wound site into the reservoir when transitioning from the first state to the second state.

8. The apparatus of claim 1, wherein the pump is a piezoelectric micropump operable to act on the cavity.

9. The apparatus of claim 1 further comprising:
   a first one-way valve permitting single direction fluid flow into the cavity and a second one-way valve permitting single direction fluid flow from the cavity to the reservoir.

10. The apparatus of claim 1, wherein the pump is adapted to operate on the cavity to provide the pressure as a predetermined pressure within the cavity when the cavity is in the first state.

11. The apparatus of claim 1 further comprising:
   a conduit in fluid communication with the input of the cavity and adapted for conveying exudate from the wound site to the input of the cavity.

12. The apparatus of claim 11 further comprising:
   a dressing attachable in fluid communication with the wound site of the patient and the conduit.

13. An apparatus for controlling flow of fluid exudate from a wound site of a patient comprising:
   a sealed chamber;
   a passive pump unit, disposed in the sealed chamber, the passive pump unit including a cavity having an input for receiving the exudate from the wound site of the patient conveyed over a conduit connectable in fluid, communication with the input, and an output for providing the received exudate from the cavity to a reservoir, the cavity comprising a non-rigid, deformable wall opposing a rigid, non-deformable plate, wherein the sealed chamber is in fluid communication with the deformable wall and wherein the input of the cavity is not positioned at the deformable wall or the non-deformable plate; and
   an actuator element, disposed, in the sealed chamber, the actuator element operable to create a fluid pressure within the sealed chamber and to apply the fluid pressure to the deformable wall of the cavity for drawing the fluid exudate from the wound site through the conduit and the input and into the cavity, the actuator element adapted to apply a fluid pressure to the non-rigid, deformable wall of the cavity in the direction of the rigid, non-deformable plate to transition the cavity from a first state to a second state; wherein the cavity is adapted to hold the received exudate without the received fluid exudate flowing through the input and the output and to provide the received exudate from the cavity through the output to the reservoir without the received exudate flowing through the input.

14. The apparatus of claim 13, wherein the actuator element is at least one of mechanically and electrically operable to create the fluid pressure.

15. The apparatus of claim 13, wherein the cavity is deformable to draw the exudate from the wound site when the cavity recovers an original form following deformation of the cavity.

16. The apparatus of claim 13, wherein, when the pressure is created in the cavity by the actuator element and the cavity contains the received fluid exudate, the received exudate in the cavity is caused to flow through the output without flowing through the input.

17. The apparatus of claim 13, wherein the actuator element is operable to create a vacuum within the cavity while the cavity is pressurized by the actuator element for drawing the exudate from the wound site through the input and into the cavity.

18. The apparatus of claim 13, wherein the actuator element is operable to act on the pump unit to create at least one of a continuous and varying fluid pressure within the cavity for drawing the exudate from the wound site through the input and into the cavity.

19. The apparatus of claim 13, wherein the conduit is part of the apparatus and has a first end connected to the input.

20. The apparatus of claim 13 further comprising:
   a dressing attachable in fluid communication with the wound site of the patient and the input.

21. The apparatus of claim 13 further comprising:
   the reservoir attachable in fluid communication with the output of the cavity.

22. The apparatus of claim 1, wherein a distance between the non-rigid, deformable wall and the rigid, non-deformable plate in the second state is H1 and a distance between the non-rigid, deformable wall and the rigid, non-deformable plate in the first state is H2, and H1 is greater than H2.

23. The apparatus of claim 13, wherein there is a relationship between pressure within the cavity and a distance between the non-rigid, deformable wall, and the rigid, non-deformable plate.

* * * * *

UNITED STATES PATENT AND TRADEMARK OFFICE
CERTIFICATE OF CORRECTION

PATENT NO. : 10,780,200 B2  
APPLICATION NO. : 13/992623  
DATED : September 22, 2020  
INVENTOR(S) : Landy Aaron Toth Page 1 of 1

It is certified that error appears in the above-identified patent and that said Letters Patent is hereby corrected as shown below:

In the Claims

In Column 11, Line 2, Claim 1: replace --flow of thud-- with --flow of fluid--.
In Column 11, Line 25, Claim 1: replace --force fluid-- with --fluid--.
In Column 12, Line 1, Claim 13: replace --fluid exudate-- with --exudate--.
In Column 12, Line 7, Claim 13: replace --fluid,-- with --fluid--.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*